United States Patent
Sterling

[11] Patent Number: 5,817,088
[45] Date of Patent: Oct. 6, 1998

[54] LASER INDIRECT OPHTHALMOSCOPE

[75] Inventor: William D. Sterling, Fremont, Calif.

[73] Assignee: Nidek Incorporated, Fremont, Calif.

[21] Appl. No.: 797,342

[22] Filed: Feb. 10, 1997

[51] Int. Cl.⁶ ............................... A61F 9/007; A61B 3/10
[52] U.S. Cl. ............................................... 606/4; 351/205
[58] Field of Search ................... 606/4, 10, 13, 606/17, 18; 351/205, 214

[56] References Cited

U.S. PATENT DOCUMENTS

| | | |
|---|---|---|
| 5,243,368 | 9/1993 | Kosuke et al. . |
| 5,252,999 | 10/1993 | Sukigara et al. ..................... 351/205 |
| 5,279,298 | 1/1994 | Flower . |
| 5,295,989 | 3/1994 | Nakamura . |
| 5,300,062 | 4/1994 | Ueno . |
| 5,311,224 | 5/1994 | Enomoto . |
| 5,347,329 | 9/1994 | Ota . |
| 5,404,184 | 4/1995 | Koike et al. . |
| 5,423,798 | 6/1995 | Crow . |
| 5,425,729 | 6/1995 | Ishida et al. . |
| 5,442,487 | 8/1995 | Mizuno . |
| 5,450,144 | 9/1995 | Ben Nun . |
| 5,488,443 | 1/1996 | Ota et al. . |
| 5,506,634 | 4/1996 | Wei et al. . |
| 5,548,352 | 8/1996 | Dewey . |

*Primary Examiner*—Jennifer Bahr
*Assistant Examiner*—Eric F. Winakur
*Attorney, Agent, or Firm*—Harris Zimmerman

[57] ABSTRACT

A binocular indirect ophthalmoscope having an improved delivery system for a laser treatment beam includes a laser beam generator directed horizontally across the pupillary line of one eye path of the binocular arrangement. A single beamsplitter is placed directly in the one eye path to receive the laser beam and deflect it toward the visualized target. The beamsplitter is coated to reflect 90–100% of the laser beam, so that reflectivity of and visibility through the beamsplitter is optimized. A beam trap is disposed to receive the transmitted portion of the laser beam. Separate protective filters for laser protection of each eye of the physician are optimized for protection and visible throughput without limitations imposed by a combined beamsplitter function. The position of the beamsplitter in the optical axis of one eye eliminates losses in the illumination path. Because the treatment beamsplitter and safety filter functions are separated and optimized, one eye of the physician is provided with a visual pathway that is substantially unobstructed by loss-generating optical elements, enhancing the visibility of the aiming beam.

20 Claims, 4 Drawing Sheets

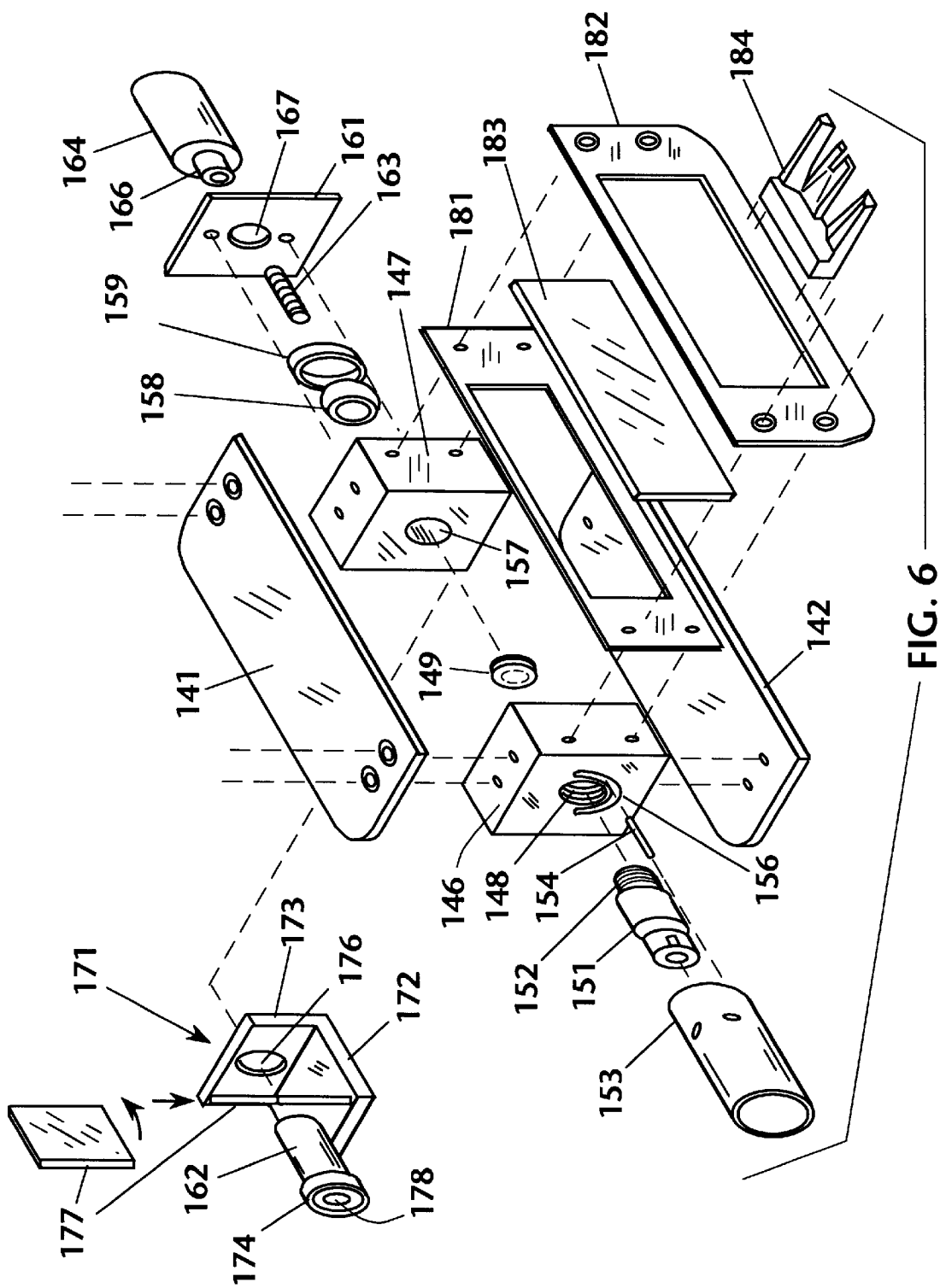

LASER INDIRECT OPHTHALMOSCOPE

BACKGROUND OF THE INVENTION

This invention relates to binocular indirect ophthalmoscopes, and, more particularly, to a binocular indirect ophthalmoscope having an improved laser treatment system associated therewith.

Laser treatment of disorders of the eye has been well-developed in the prior art, due in part to the fact that the eye is transparent to many optical wavelengths and is uniquely suited to receive diagnostic and therapeutic radiation to internal structures in a non-invasive manner. Indeed, ophthalmic laser systems were among the first medical laser systems to be developed to exploit this unique property.

The basic non-invasive or transpupillary laser delivery system is based on the slit lamp biomicroscope or "slit lamp". The slit lamp is arranged to allow easy illumination and microscopic viewing of the eye. The basic design common to all slit lamps and slit lamps modified for laser surgery includes a high brightness illuminator and microscope which are mounted on a common rotational axis, with each subsystem aimed at the same point on the rotational axis. This arrangement allows the viewing angle of the microscope and illuminator to be changed as often as desired without moving the field of illumination or view.

The slit lamp laser delivery system has a few disadvantages as well. The primary disadvantage is that the microscope and illuminator are large and, when combined with the supporting mechanical structure, form a device which is difficult to move. The slit lamp is normally mounted to direct the optical path into a horizontal plane in order to see into the eye of a seated patient. This arrangement is not suited for treating or examining small infants or bed-ridden patients. The slit lamp systems are also severely limited in their ability to treat patients with detached retinas and other conditions where, in conjunction with gravity, gas or dense fluids that have been introduced into the eye to move and secure detached tissues prior to laser exposure, therapy requires orienting the patients head to reposition the tissue or tamponade material.

A second type of laser delivery system has been developed to permit the examination and treatment of patients with substantial positional freedom, thus overcoming the limitations of the slit lamp devices noted above. The binocular indirect ophthalmoscope is a device worn on the physician's head and includes a telescopic device and illuminator which may be combined with a laser beam projection system. This device may be operated in any orientation, and permits access to bed-ridden patients and small infants. The organizing principle is that the viewing, illumination, and laser beam axes are combined by directing each optical path from different angular positions, not necessarily in the same plane, and directing them to a common point of intersection. Moreover, the optical pathways are arranged within a cone sufficiently narrow to project through the pupil of the eye.

To achieve the narrow cone effect, the telescope system employs a combination of mirrors or prisms to move the optical path of each of the physician's eyes from a normal anatomic separation of approximately 60 mm to approximately 15 mm. This arrangement permits binocular visualization of the interior of the patient's eye by both eyes of the physician at a reasonable working distance of 200–700 mm.

Physical and physiological factors combine to create design problems in existing laser binocular indirect ophthalmoscopes. The unit must be lightweight and supported on the head of the physician therefore it must be lightweight and the components must be arrayed within a small area around the physician's eyes and forehead. The viewing optics must be provided with a filter to block the laser treatment beam and protect the physician's eyes, and an aiming beam must be provided to indicate to the physician the focal spot of the laser treatment beam within the patient's eye.

Generally speaking, the illuminator device must have a broad field to illuminate the eye interior uniformly, and it is preferably centered with respect to the physician's eyes. If the laser beam is introduced by a small mirror that is centrally located, it is necessarily disposed within the illumination path and may block as much as 30%–60% of the illuminating light. If the laser beam mirror is placed too far off the illumination axis, to permit full illumination, it becomes very difficult to simultaneously illuminate, view, and treat the eye through a small pupillary opening.

The laser beam may be introduced into the visual path by a beamsplitter which is highly reflective of the treatment laser wavelength and partially reflective of the aiming beam wavelength. The beamsplitter extends across the binocular visual pathway and also serves as a safety filter to protect the physician's eyes. The difficulty with this design is that the filter is large and it greatly darkens the view of the physician by its transmission characteristic, blocking either the visual or illumination path or both. Also, since the beamsplitter must reflect the aiming beam into the patient's eye and also some fraction of the aiming beam through the same piece to the physician's eye the result is either a poorly visible aiming beam for the physician or an extremely bright aiming beam delivered into the patient's eye to compensate for the filter losses.

One solution to degradation of visualization caused by the use of a beamsplitter is the provision of an electro-mechanical system to move the safety filter into place only when the laser treatment beam is about to be fired. Such systems, a reversal of single lens reflex camera systems that flip the mirror out of the optical axis to expose the film, are heavy, complex, and prone to malfunction.

SUMMARY OF THE PRESENT INVENTION

The present invention generally comprises a binocular indirect ophthalmoscope having an improved delivery system for a laser treatment beam, whereby illumination, visualization, and treatment are enhanced.

The apparatus of the invention includes a binocular indirect ophthalmoscope arrangement adapted to be supported on the head of the physician, as is generally known in the prior art. A laser beam generator is directed horizontally across the pupillary line of one eye path of the binocular arrangement, and a single beamsplitter is placed directly in the one eye path to receive the laser beam and deflect it toward the visualized target. The beamsplitter is coated to reflect 90–100% of the laser beam, so that reflectivity of and visibility through the beamsplitter are optimized. A beam trap is disposed to receive the transmitted portion of the laser beam. Laser protection of each eye of the physician may be achieved by the provision of separate protective filters which are optimized for protection and visible throughput without limitations imposed by a combined beamsplitter function. The position of the beamsplitter in the optical axis of one eye eliminates losses in the illumination path. Because the treatment beamsplitter and safety filter functions are separated and optimized, the need for moving filter systems is eliminated, while one eye of the physician is provided with a visual pathway that is substantially unobstructed by loss-generating optical elements.

BRIEF DESCRIPTION OF THE DRAWING

FIG. 6 is an exploded perspective view of another embodiment of the treatment beam delivery assembly of the laser binocular indirect ophthalmoscope.

DESCRIPTION OF THE PREFERRED EMBODIMENT

Figure 1:
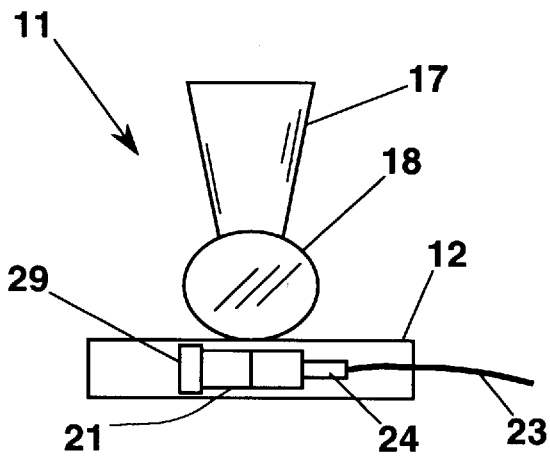
FIG. 1 is a front elevation of the basic components of the laser binocular indirect ophthalmoscope of the present invention.
Figure 2:
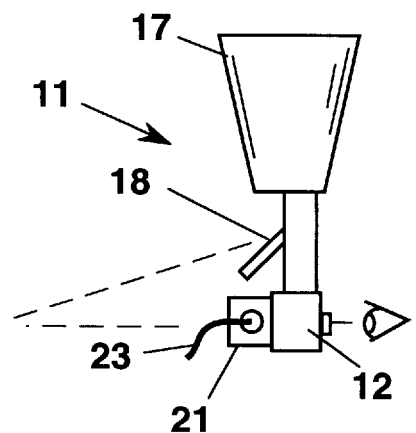
FIG. 2 is a side elevation of the laser binocular indirect ophthalmoscope as shown in FIG. 1.
Figure 3:
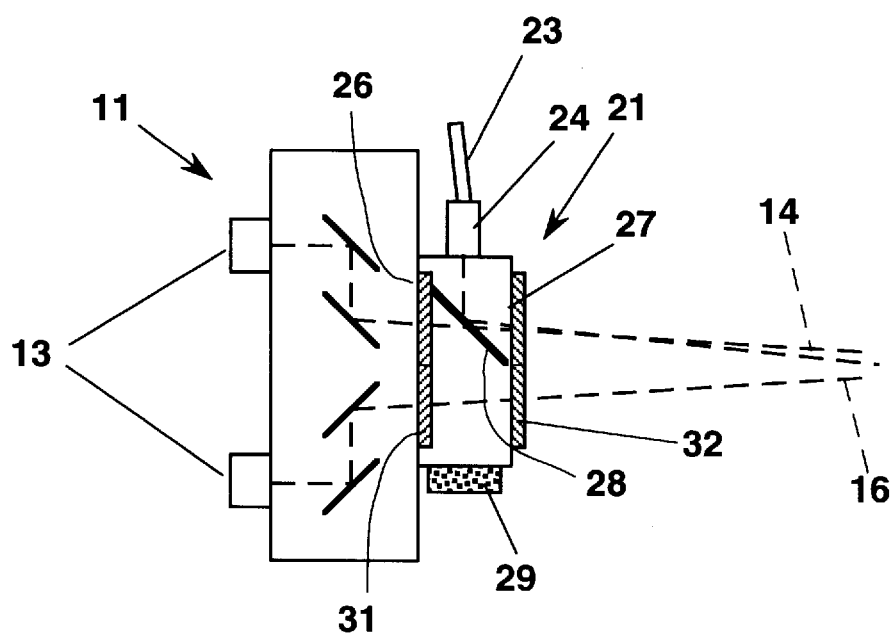
FIG. 3 is a schematic view of the laser binocular indirect ophthalmoscope as shown in FIGS. 1 and 2.

The present invention generally comprises a binocular indirect ophthalmoscope having an improved arrangement for delivering a laser treatment beam. With regard to FIGS. 1–3, the major components of the ophthalmoscope system 11 include a housing 12 enclosing a binocular telescope 13 for visualizing the interior of a patient's eye. The binocular telescope employs a combination of mirrors or prisms to move the optical path of each of the physician's eyes from a normal anatomic separation of approximately 60 mm to approximately 15 mm, and to converge the two optical paths 14 and 16, whereby a target within the narrow opening of the pupil of the patient's eye may be visualized. The objective and image-forming lenses of the binocular telescope are not shown, but conform to arrangements generally known in the prior art. Disposed superjacently of the housing 12 and generally centered with respect to the visual pathways 14 and 16 is an illumination source 17 which is directed to an obliquely oriented mirror 18. The mirror 18 directs the illumination beam generally medially of the visual pathways 14 and 16 to illuminate the visualized target area.

A salient aspect of the invention is the provision of a laser beam generator 21 for providing a tissue treatment beam as well as an aiming or pilot beam. The device 21 is incorporated within a housing 22 which may comprise an integral portion of the system 11 or a separate device that is retrofitted onto an existing binocular indirect ophthalmoscope. An optical fiber assembly 23 is joined to the housing 22 by a focusing coupling 24, the optical fiber extending to a laser which supplies a high power treatment beam and a low power aiming beam. The coupling forms a laser beam directed generally horizontally across the pupillary line of one eye path, for example visual path 14. The housing further includes a proximal window 26 and a distal window 27, through which the visual pathways 14 and 16 extend. A beamsplitter 28 is located within the housing 21 and disposed in one of the visual pathways; for example, as shown in the Figures, the visual pathway 14 of the left eye of the physician. The beamsplitter 28 is oriented to reflect the laser aiming and treatment beam from the coupling 24, whereby the laser beam is directed generally along an axis that is coincident and converging with the visual pathways 14 and 16 and the illumination pathway. The beamsplitter 28 is coated to reflect 90–100% of the laser beam, so that reflectivity of and visibility through the beamsplitter is optimized. A laser beam trap 29 is disposed at a side of the housing 21 opposite the coupling 24 to receive and squelch the small proportion of laser radiation that passes through the beamsplitter 28.

The device 11 further includes a pair of filter assemblies 31 and 32 disposed in the windows 26 and 27, respectively, of the housing 21. Each filter assembly may include bilaterally distinct bandpass characteristics to compensate for the placement of the beamsplitter 28 in the visual path of one of the eyes. The bilateral differential in filter bandpass serves to equalize the brightness and clarity experienced by both eyes of the physician, while also reducing the filtering effect in the visual path having the beamsplitter 28.

Figure 4:
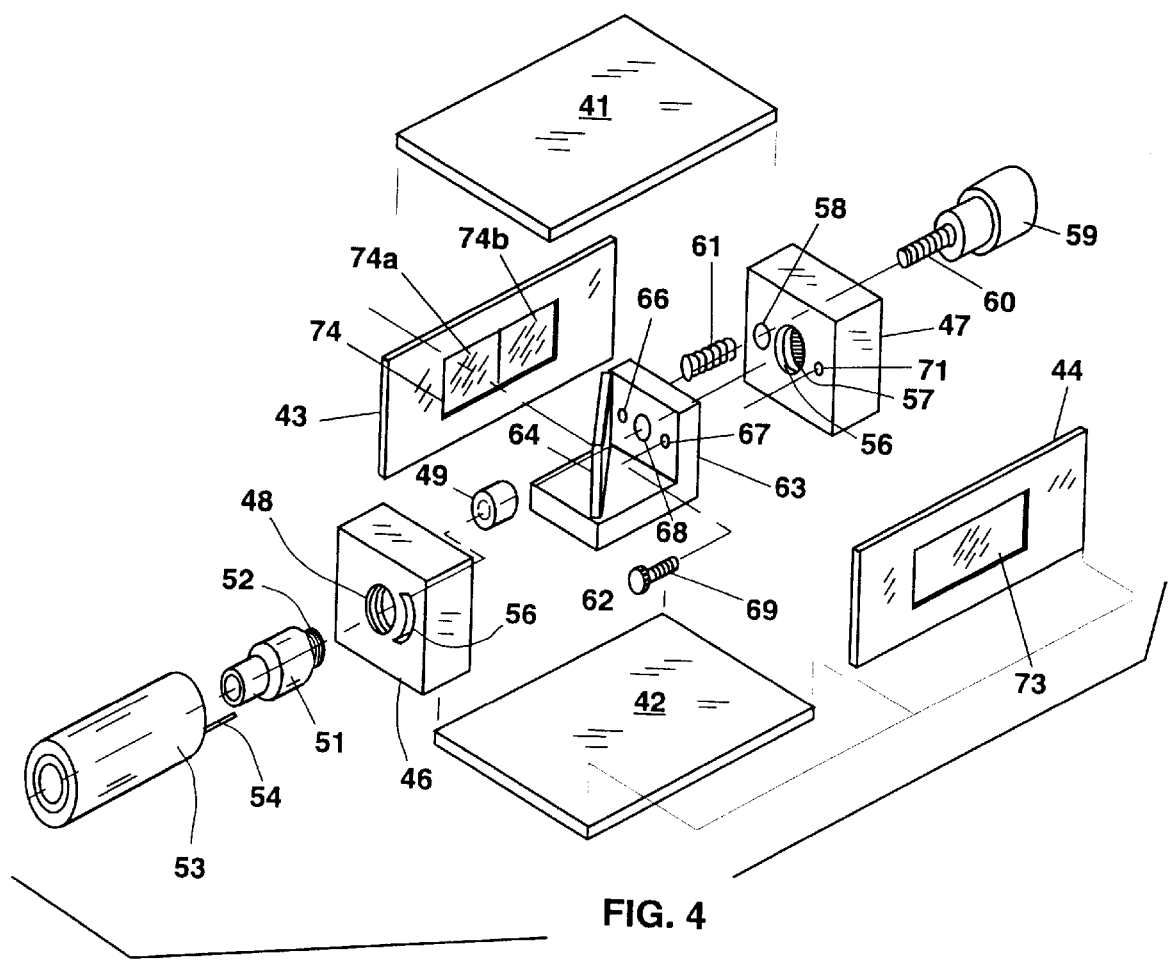
FIG. 4 is an exploded perspective view of the treatment beam delivery assembly of the laser binocular indirect ophthalmoscope of the present invention.

With regard to FIG. 4, one embodiment of the assembly of the device 21 includes upper and lower plates 41 and 42, both generally rectangular and disposed in vertically spaced, parallel relationship. Front and rear filter plates 43 and 44 are secured between the upper and lower plates. Likewise, end blocks 46 and 47 are secured between the upper and lower plates, whereby the upper and lower plates, filter plates, and end blocks form an enclosure secured by screws (not shown) or the like. End block 46 includes a threaded port 48, with a lens 49 mounted in the inner end thereof. An optical fiber fitting 51 includes a threaded end 52 received in the threaded port 48, and includes an axially extending bore in which an optical fiber extends and is terminated. The fitting 51 is secured within a sleeve 53 for rotation in common therewith. The sleeve 53 may be rotated manually to translate the terminal end of the optical fiber with respect to the lens 49, whereby the lens may form and focus a beam of coherent light carried by the optical fiber from a laser source. A limit pin 54 extends from the inner end of the sleeve 53 generally parallel to the axis thereof, and is received freely in an arcuate groove 56 formed in the outer face of the end block 46 and subtending a partial arc about the port 48. The pin 54 riding in the groove 56 confines rotation of the sleeve 53 and thus limits the focal range of lens 49.

The other end block 47 is provided with a large central recess 57 which is disposed generally coaxially with the optical axis of the lens 49. An actinic radiation absorbing material 56 is disposed within the recess 57 to receive and absorb the wavelength of the laser light conducted through the optical fiber to the end block 46, thus forming a laser beam trap. A hole 58 extends through the block adjacent to the recess 57, and an adjustment knob 59 includes a threaded end 60 protruding through the hole 58. A beamsplitter mount 62 includes an end plate 63, and a beamsplitter 64 is supported by the end plate 63 and the base of the mount 62. The beamsplitter 64 comprises a transparent planar optical member having a front surface coated to reflect the laser wavelength. The end plate 63 includes a central optical opening 68, through which the unreflected portion of the laser beam may pass, and a pair of threaded screw holes 66 and 67 flanking the opening 68.

The threaded hole 66 is disposed to engage the threaded end 60 of the adjustment know 59, whereby the spacing of the beamsplitter mount 62 from the end block 47 may be selectively varied by rotation of the adjustment knob 59. A spring 61 is received about the threaded end 60 and compressed between the end plate 63 and end block 47, whereby the beamsplitter mount 62 is resiliently biased away from the end block 47. An angular adjustment screw 69 extends through hole 67 in end plate 63 and is engaged in tapped hole 71. The screw 69 may be rotated to selectively vary the angular relationship of the end plate 63 with respect to the end block 47, and thus alter the angular disposition of the beamsplitter 64. The screws 61 and 69 and the spring 61 are disposed to be clear of the visual pathways of the binocular indirect ophthalmoscope.

The filter plate 44 includes a centrally located filter window 73 formed of a transparent material having a passband that excludes the wavelength of the actinic radiation of the laser treatment beam. Filter plate 43 includes a centrally located filter window 74 having bilaterally adjacent filter segments 74a and 74b, each placed in respective left and right visual paths of the binocular indirect ophthalmoscope. As described previously, the beamsplitter 64 is oriented in the left visual path, whereby the laser beam is reflected along the same general axis as the left visual path. The adjustment knob 69 selectively adjusts the axial spacing of the laser beam and the visual path, and the adjustment screw 69 selectively varies the angular convergence of the laser beam with respect to the visual path. The focus of the laser beam is controlled by the sleeve 53. The segment 74a is selected to compensate for the imposition of the beamsplitter 64 in the respective visual path, while the segment 74b is selected only for passband characteristics, whereby the brightness and clarity experienced by both eyes of the physician may be substantially equalized.

Figure 5:
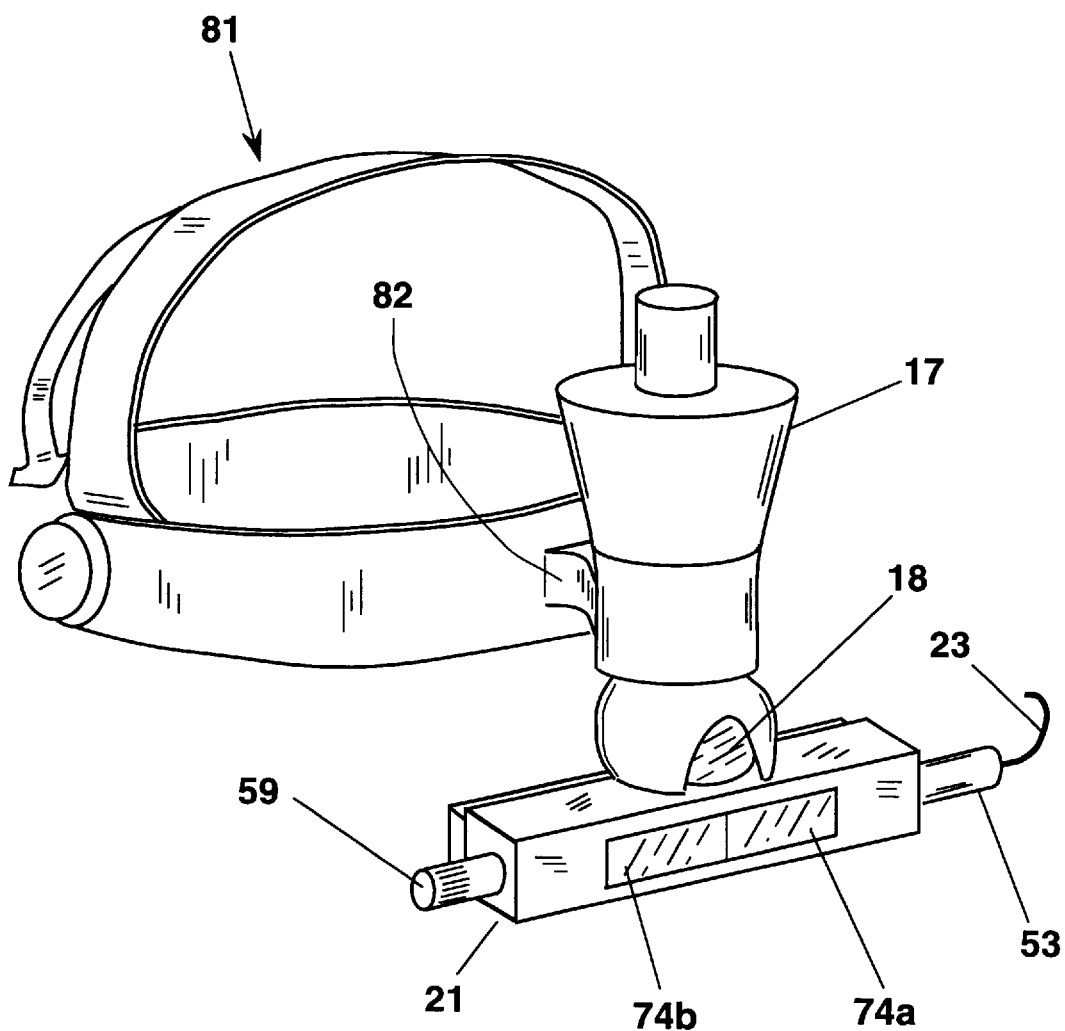
FIG. 5 is a perspective view of a laser binocular indirect ophthalmoscope incorporating the treatment beam delivery system of the present invention.

The invention as depicted in FIGS. 1–4 may be operatively associated with a binocular indirect ophthalmoscope as shown in FIG. 5. The binocular indirect ophthalmoscope includes a headgear assembly 81 for supporting the device on the head of the physician, and a bracket 82 joins the illumination assembly 17 to the headgear assembly 81 to support the binocular indirect ophthalmoscope generally adjacent to the forehead of the physician. It may be appreciated that the illumination beam emanating from the reflector 18 is completely unimpeded by the introduction of the laser treatment beam, which enters the device 21 at the sleeve 53.

With regard to FIG. 6, a further embodiment of the assembly of the device 21 includes upper and lower plates 141 and 142, both generally rectangular and disposed in vertically spaced, parallel relationship. The plates 141 and 142 are assembled to a lens block 146 and a ball joint housing 147 at opposed ends of the plates by appropriate screw fasteners. Lens block 146 includes a threaded port 148, with a lens 149 mounted in the inner end thereof. An optical fiber fitting 151 includes a threaded end 152 received in the threaded port 148, and includes an axially extending bore in which an optical fiber extends and is terminated. The fitting 151 is secured within a sleeve 153 for rotation in common therewith. The sleeve 153 may be rotated manually to translate the terminal end of the optical fiber with respect to the lens 149, whereby the lens may form and focus a beam of coherent light carried by the optical fiber from a laser source. A limit pin 154 extends from the inner end of the sleeve 153 generally parallel to the axis thereof, and is received freely in an arcuate groove 156 formed in the outer face of the lens block 146 and subtending a partial arc about the port 148. The pin 154 riding in the groove 156 confines rotation of the sleeve 153 and thus limits the focal range of lens 149.

The ball joint housing 147 is similar in size to the lens block, and includes a large central passage 157 extending therethrough and aligned generally along the optical axis of the lens 149. A ball articulation 158 and complementary friction ring 159 are secured in the outer end of the passage 157, and are retained therein by a pressure plate 161. A ball coupling 162 extends into the inner end of the passage 157, and is secured to a threaded rod 163 extending from the coupling 162 through the ball 158 and ring 159. An adjustment knob 164 includes a tapered end 166 extending through an opening 167 in the pressure plate 161 to be secured to the threaded rod 163. As is known in the prior art, the adjustment knob 164 may be unthreaded slightly from the rod 163 and moved manually to adjust the angular disposition of the ball coupling 162, and then retightened on the rod 163 to impinge on the pressure plate 161 and immobilize the ball coupling in a desired angular disposition.

A beamsplitter mount 171 includes a base panel 172 and an end panel 173. The ball coupling 162 is provided with a flanged end 174 which is dimensioned to be secured in an opening 176 in the end panel 173. A planar front surface reflecting member 177 is supported by the base panel 172 and end panel 173, and disposed to intersect the optical axis of the lens 149, whereby the laser beam formed by the lens 149 is reflected outwardly from the device 21. Moreover, the end face of the flanged end 174 is provided with a beam trap orifice 178 which is aligned generally with the optical axis of the lens 149, whereby all optical energy from the beam that passes through the beamsplitter is received and absorbed within the beam trap orifice 178. Thus the ball coupling provides both support and angular adjustment, as well as absorption of non-reflected laser energy.

The beamsplitter mount 171 is supported solely by the ball joint assembly, so that the angle of the reflecting member 177 may be adjusted within an appropriate range by use of the adjustment knob 164, as explained above.

Also secured to the lens block 146 and ball joint housing 147 are an inner filter plate 181 and outer filter plate 182, both extending between the lens block and the ball joint housing and spanning the distance between the top and bottom plates 141 and 142 An eye protection filter assembly 183 is secured between the inner and outer filter plates 181 and 182 to selectively block the narrow band surrounding the laser wavelength and pass the remaining portions of the visible spectrum. The filter assembly 183 may comprise a bilateral differential passband filter, as described previously, or it may provide the same filter effect in both binocular visual pathways.

The assembly of FIG. 6 may further include a dovetail spade lug 184 for engaging a complementary-formed bracket joined to a standard binocular indirect ophthalmoscope The introduction of the laser aiming and treatment beam into the visual pathway of a single eye of the binocular indirect ophthalmoscope provides the following general advantages:

1) The separation and separate optimization of the beam splitting mirror and the laser protective filter systems;

2) The improvement of aiming beam visibility in a binocular viewing system by providing one of the two eyes with a pathway that is substantially unobstructed by lossy optical components;

3) Full illumination of the interior of the eye by the binocular indirect ophthalmoscope illumination system with no diminution by the laser beam projector system;

4) Minimization of the convergence angles of the visual pathways, laser beam, and illumination beam, whereby narrower pupil diameters may be accessed successfully; and, 5) Complete enclosure of the laser beam delivery system, reducing problems of contamination and cleanliness.

The elements of the invention may be provided as a device that is retrofitted onto an existing binocular indirect ophthalmoscope, or may be incorporated integrally in a laser binocular indirect ophthalmoscope.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

I claim:

1. In a binocular indirect ophthalmoscope having two binocular visual pathways to visualize an ophthalmic visual target, the improvement comprising:

a treatment beam light source; and, means for directing a treatment beam coaxially with one of the two binocular visual pathways toward the ophthalmic visual target.

2. The improved binocular indirect ophthalmoscope of claim 1, wherein said treatment beam light source includes an optical fiber delivery system having an output end joined to said binocular indirect ophthalmoscope.

3. The improved binocular indirect ophthalmoscope of claim 2, wherein said treatment beam light source includes means for receiving light from said optical fiber delivery system and forming a treatment beam.

4. The improved binocular indirect ophthalmoscope of claim 3, wherein said means for directing a treatment beam includes beamsplitter means interposed in said one visual pathway and disposed to receive said treatment beam.

5. The improved binocular indirect ophthalmoscope of claim 4, wherein said treatment beam is substantially monochromatic, and said beamsplitter means includes means for reflecting the wavelength of said treatment beam and transmitting other wavelengths in the visible light range.

6. The improved binocular indirect ophthalmoscope of claim 5, further including protective filter means interposed in said two visual pathways to protect the eyes of the ophthalmoscope operator.

7. The improved binocular indirect ophthalmoscope of claim 6, wherein said protective filter means includes bilateral differential filter means to compensate for the interposition of said beamsplitter means in said one visual pathway.

8. The improved binocular indirect ophthalmoscope of claim 7, wherein said bilateral differential filter means includes first and second light filters disposed in said two visual pathways, said first and second light filters having substantially differing bandpass characteristics.

9. The improved binocular indirect ophthalmoscope of claim 8, further including a closed housing for enclosing said optical fiber delivery system, said means for receiving light and forming a treatment beam, said beamsplitter means, and said first and second light filters.

10. The improved binocular indirect ophthalmoscope of claim 3, wherein said means for receiving includes a first end plate having a port extending therethrough, and a beam-forming lens assembly mounted in operative association with said port.

11. The improved binocular indirect ophthalmoscope of claim 10, wherein said means for receiving further includes an optical fiber coupler secured to said output end and disposed in said port, and means for varying the distance between said output end and said lens assembly.

12. The improved binocular indirect ophthalmoscope of claim 5, wherein said means for reflecting includes a planar optical component having a reflective front surface adapted to reflect said wavelength of said treatment beam.

13. The improved binocular indirect ophthalmoscope of claim 12, further including a mounting block, said optical component secured to said mounting block in an angular relationship which reflects said treatment beam from said beam forming means to extend along said one visual pathway.

14. The improved binocular indirect ophthalmoscope of claim 13, further including means for selectively varying said angular relationship to adjust the position of said treatment beam with respect to the ophthalmic visual target.

15. The improved binocular indirect ophthalmoscope of claim 14, further including beam trap means disposed on an optical axis extending to said beam forming means to receive and absorb light passing through said planar optical component.

16. The improved binocular indirect ophthalmoscope of claim 14, wherein said means for selectively varying said angular relationship includes swivel means for supporting said mounting block.

17. The improved binocular indirect ophthalmoscope of claim 16, wherein said swivel means includes a ball coupling secured to said mounting block, and an articulated ball disposed to engage said ball coupling, and adjustment knob means connected to said ball coupling for manually adjusting the angular disposition of said mounting block.

18. The improved binocular indirect ophthalmoscope of claim 17, wherein said treatment beam is emitted along a beam axis from said treatment beam light source, and said ball coupling includes a treatment beam trap orifice disposed generally coaxially with said beam axis to receive treatment beam energy transmitted through said means for reflecting.

19. A method for coupling a laser treatment beam to a binocular indirect ophthalmoscope having two visual binocular visual pathways to visualize an ophthalmic visual target, including the steps of:

connecting an optical fiber delivery system from a laser light source to a treatment beam-forming assembly in said binocular indirect ophthalmoscope;

interposing a beamsplitter in one of the visual pathways of the binocular indirect ophthalmoscope; and, directing the treatment beam to impinge on the beamsplitter and be reflected along the one visual pathway toward the ophthalmic target.

20. The method of claim 19, further including the step of providing a pair of protective light filters for the two visual pathways, said pair of protective light filters having differing filter characteristics adapted to compensate for the imposition of the beamsplitter in the one visual pathway.

* * * * *